United States Patent [19]

Rauleder et al.

[11] Patent Number: 5,107,009

[45] Date of Patent: Apr. 21, 1992

[54] PROCESS FOR THE PREPARATION OF MERCAPTOSILANES

[75] Inventors: Hartwig Rauleder; Claus-Dietrich Seiler; Hans-Joachim Kötzsch; Burkhard Standke, all of Rheinfelden, Fed. Rep. of Germany

[73] Assignee: Hüls Aktiengesellschaft, Marl, Fed. Rep. of Germany

[21] Appl. No.: 738,348

[22] Filed: Jul. 31, 1991

[30] Foreign Application Priority Data

Aug. 16, 1990 [DE] Fed. Rep. of Germany ....... 4025866

[51] Int. Cl.$^5$ ................................................. C07F 7/08
[52] U.S. Cl. ..................................................... 556/429
[58] Field of Search ......................................... 556/429

[56] References Cited

U.S. PATENT DOCUMENTS

| Re. 28,129 | 8/1974 | Rahus et al. | 556/429 |
| 3,590,065 | 6/1971 | Rahus et al. | 556/429 |
| 4,082,790 | 4/1978 | Speier | 556/429 |
| 4,556,724 | 12/1985 | Seiler et al. | 556/429 |

FOREIGN PATENT DOCUMENTS 0156794 6/1988 Japan ................................. 556/429

*Primary Examiner*—Paul F. Shaver
*Attorney, Agent, or Firm*—Felfe & Lynch

[57] ABSTRACT

Mercaptosilanes are prepared from haloorganylsilyl compounds and an alkali metal hydrogen sulfide in the presence of a polar, aprotic medium.

7 Claims, No Drawings

PROCESS FOR THE PREPARATION OF MERCAPTOSILANES

FIELD OF THE INVENTION

This invention relates to a novel process for the preparation of mercaptosilanes which comprises reacting the corresponding haloorganylsilane compounds with an alkali metal hydrogen sulfide in the presence of a polar, aprotic medium.

BACKGROUND OF THE INVENTION

German Auslegeschrift 20 35 619 and U.S. Pat. No. 3,590,065 disclose that mercaptosilanes can be prepared in a single-step reaction by reacting haloorganylsilane compounds suitable for this reaction with thiourea and ammonia. However, this method has the disadvantage that, for the achievement of economically acceptable reaction rates, long reaction periods of more than 24 hours are required. The yields which can be achieved by using this method vary and reach values only between 75 and 80%, based on the reacted amount of the haloorganylsilane compound which is used. Furthermore, this method is burdened with an unavoidable formation of guanidine hydrochloride, the separation of which requires additional equipment, labor and cost.

An attempt was made to improve the method described in U.S. Pat. No. 3,590,065. By adding reaction accelerators to the mixture of reactants, a reduction of the reaction times to about 6 hours was achieved. However, relative to the yields and reaction temperatures to be applied, no improvements were obtained (see U.S. Pat. No. 4,401,826).

Processes for the preparation of mercaptosilanes by reaction of corresponding thioacetosilane compounds with alcohols have not acquired any technical importance because of low yields and limited applicability of this method (see U.S. Pat. No. 3,632,826; 3,565,937; 3,565,935; and German Auslegeschrift 20 38 715).

Processes for the preparation of mercaptosilanes which start, for example, from thiopropionic acid amide silanes and convert the same by hydrogenation under pressure into the corresponding mercaptosilanes have not acquired any technical importance either, because the yields obtained therefrom are unsatisfactory (see European Patent 0 018 094). Likewise, attempts to hydrogenate cyanoalkylsilane compounds in the presence of elemental sulfur or hydrogen sulfide to obtain mercaptosilanes produced no satisfactory results with respect to yields (see U.S. Pat. No. 4,012,403).

It has also been attempted to prepare mercaptosilanes by selective cleavage of special thioethersilanes with the aid of Friedel-Crafts catalysts. This method of preparation, however, is not economically feasible because of the expensive preparation of the corresponding precursors (see German Patent 23 40 886).

The preparation of mercaptosilanes by reacting the corresponding haloorganylsilane compounds with hydrogen sulfide in the presence of ethylenediamine and large amounts of heavy metal sulfides leads to the formation of diverse by-products which are difficult to separate from the target product and lead to a two-phase raw product system, the work-up of which is burdened with the problems described in German Patent 33 46 910 (see also U.S. Pat. No. 3,849,471).

Certain improvements over the method of preparation described in U.S. Pat. No. 3,849,471 were obtained when the reaction of the starting silanes with hydrogen sulfide was not performed in the presence of diamines but in the presence of ammonia, primary, secondary or tertiary amines, and optionally also in the additional presence of polar, protic or aprotic media (see U.S. Pat. No. 4,082,790). This method of preparation has the disadvantage that, in order to achieve the reaction temperatures which are required for the reaction of the reactants, the reactions must be performed in an autoclave. If the reactions are performed in the absence of polar media, uneconomically long reaction periods have to be accepted in order to achieve acceptable rates of reaction. The addition of polar media to the mixture of reactants also results in only minor reductions of the reaction periods; however, because of the increased solubility of the hydrochlorides which are formed as by-products of the reaction, all the difficulties arise which are mentioned in German Patent 33 46 910 and which can be remedied only by means of corresponding costly measures, whereby the process is additionally burdened.

The preparation of mercaptosilanes by reacting hydrogen sulfide with ethylenic unsaturated silanes with the aid of ultraviolet light or in the presence of metals of the eighth side group of the Periodic System leads to small yields of target product; the reaction, moreover, is impaired by the formation of substantial amounts of by-products (see U.S. Pat. No. 3,890,312 and German Auslegeschrift 10 00 817).

British Patent 1,102,251 discloses the reaction of alkali metal hydrogen sulfides with haloalkylsilanes in a methanolic medium to form the corresponding mercaptosilanes. This method of preparation, however, requires extraordinarily long reaction periods in order to achieve high reaction rates, and the yields which are obtained are unsatisfactory. An improvement of the process is achieved with respect to shortening of the reaction period and increasing the yield if the reaction is allowed to proceed while simultaneously introducing hydrogen sulfide. However, the raw product work-up with respect to the removal of the hydrogen sulfide which is dissolved in the reaction mixture up to virtual saturation, and the difficulties arising in the distillative work-up of the reaction product due to continuous precipitation of alkali metal chlorides, remain problematic.

OBJECTS OF THE INVENTION

It is an object of the present invention to provide a process for the preparation of mercaptosilanes which excludes the disadvantages of the known methods of preparation, that is, to provide a process which uses relatively inexpensive raw materials and with small technical requirements leads to high space-time-yields, and in which the raw product work-up is not made difficult by salts which crystallize out and product distillates which turn cloudy.

Other objects and advantages of the present invention will become apparent as the description thereof proceeds.

DESCRIPTION OF THE INVENTION

We have discovered that the above objects are achieved by a process for the preparation of mercaptosilanes by reaction of corresponding haloorganylsilane compounds with alkali metal hydrogen sulfides, wherein the reaction of the reactants proceeds in the presence of a polar, aprotic medium.

The disadvantages of the prior art processes described above are avoided by using the method according to the present invention. Surprisingly, the reaction of the reactants proceeds within very short reaction periods and achieves high yields, which leads to extraordinarily high space-time-yields.

The process according to the present invention can be used for the preparation of mercaptosilanes of the formula

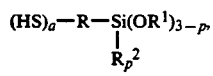

wherein
R is alkylene of 1 to 8 carbon atoms, alkarylene, arylalkylene, or aryl,
$R^1$ is alkyl of 1 to 6 carbon atoms which may be interrupted by oxygen atoms, or aryl,
$R^2$ is alkyl of 1 to 8 carbon atoms, aryl, alkaryl, or aralkyl,
p is a whole number from 0 to 3, inclusive,
a is a whole number from 1 to 3, inclusive,
or of the formula

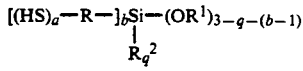

wherein
a, $R^1$ and $R^2$ have the meanings previously defined,
b is 2 or 3, and q is 0, 1 or 2,
provided the sum of b +q is equal to or less than 4.

The desired mercaptosilanes ar obtained by reacting compounds which correspond to the aforementioned formulas I and II, but wherein the HS-Group is replaced by a chlorine or bromine atom, with alkali metal hydrogen sulfides in the presence of polar, aprotic media. The following compounds are preferably prepared by the process of the present invention:
3-mercaptopropyltrimethoxysilane,
3-mercaptopropyltriethoxysilane,
3-mercaptopropylmethyldimethoxysilane,
2-mercaptoethyltriethoxysilane,
2-mercaptoethylmethyldiethoxysilane,
mercaptomethyltrimethoxysilane, and
3-mercaptopropyldimethylmethoxysilane.

The process may also be used for the preparation of compounds such as
p-mercaptophenyltrimethoxysilane,
p-(mercaptomethyl)phenyltrimethoxysilane,
2-(p-mercaptophenyl-)ethyltrimethoxysilane,
3-mercaptopropylethyldimethoxysilane,
3-mercaptopropylphenyldimethoxysilane,
3-mercaptopropyl(2-phenylethyl)dimethoxysilane,
2-mercaptoethyldimethylmethoxysilane,
3-mercaptopropyltrimethylsilane,
1,3-dimercaptopropyltrimethoxysilane,
2,4-dimercaptobutylmethyldimethoxysilane,
I,2-dimercaptoethyltrimethoxysilane,
2-(m,p-dimercaptophenyl)ethyltrimethoxysilane,
mercaptomethyldimethylmethoxysilane,
3- mercaptopropyldimethylmethoxysilane,
mercaptomethyltrimethylsilane,
di(3-mercaptopropyl)dimethoxysilane,
3-mercaptopropyl-2-mercaptoethyldimethoxysilane, and
1,2-dimercaptoethyldimethylmethoxysilane,
and the like.

In order to produce the effects according to the present invention in the preparation of mercaptosilanes by reacting the corresponding haloorganylsilane compounds with alkali metal hydrogen sulfides, the presence of those polar, aprotic compounds in the mixture of reactants which belong to the group of acid amides which are disubstituted on the nitrogen atom has proved to be especially effective. Preferred compounds within the scope of the present invention are dimethylformamide, diethylformamide, dimethylacetamide and diethylacetamide, dimethylformamide being particularly preferred. Mixtures of these substituted acid amides can also be employed.

For the course of the reaction it is not important in which sequence the reactants react with each other. The preferred form of the reaction sequence is to provide a mixture of the alkali metal hydrogen sulfide and the polar, aprotic medium, then meter in the silane and initiate the reaction of the reactants by heating the reaction mixture to a suitable reaction temperature.

The reaction may be performed continuously as well as discontinuously; the discontinuous or batch reaction is preferred. For a continuous method of operation, the suspension of the alkali metal hydrogen sulfide in a mixture of silane and polar, aprotic medium, taking into consideration the stoichiometric ratios, is introduced into a suitable reactor, for instance, into a tube reactor provided with a helix, and after a suitable residence time the reaction mixture consisting of mercaptosilane and alkali metal chloride is discharged.

The amount of polar, aprotic medium required for the performance of the process according to the present invention should be at least 50 vol.-% of the silane starting product which is used. A volume ratio of 80 to 140% is preferably used. Higher proportions of polar, aprotic medium in the mixture with the silane are not detrimental, but they make the subsequent distillative work-up of the reaction mixture more difficult.

It has proved to be advantageous to react the reaction components silane and alkali metal hydrogen sulfide in a mol ratio of 1:1. A minor excess or a deficiency of one reactant with respect to the other does not have any significant effect upon the yield based on the reaction of the particular deficient reactant. The reaction of the silane and alkali metal hydrogen sulfide is preferably performed at temperatures of 0 to 140° C. The optimum reaction temperature with respect to the yield of target product and utilization of the reaction volume varies depending upon the structure of the silane reactant which is used. We have found that if the method according to the present invention is used, the selection of the reaction temperature between 100° and 120° C. produces reaction periods which are more than 50% shorter than those of the prior art processes described hereinabove. If reaction temperatures above 120° C are used, minor yield reductions occur; when reaction temperatures below 100° C. are used, the reaction rates decrease.

A particular advantage of the process according to the present invention resides in that the reaction can be performed at normal pressure in contrast to other methods which require the use of autoclaves to bring about the reaction of the reactants. The operation at normal pressure is possible because the process of the present invention uses compounds as the sulfide reactant which neither decompose nor sublime at the required reaction temperatures.

Another surprising advantage of the method according to the present invention is that, in contrast to other methods, it makes it possible by means of a single step reaction to perform high yield mercapto substitution reactions on organosilicon compounds in which a halogen atom is in B-position to the silicon atom. It is known that in the case of substitution of such B-halogen atoms the reaction is usually accompanied by release of ethylene to varying degrees and an often spontaneous reaction to form B-elimination products which significantly reduce the yield of target product.

The mercaptosilanes obtained in accordance with the present invention are useful as bonding agents between polymers and inorganic solids, and may also be used for the modification of silicones.

The following Examples illustrate the present invention and will enable others skilled in the art to understand it more completely. It should be understood, however, that the invention is not limited solely to the particular Examples given below.

A) Comparative Examples

EXAMPLE 1

2,000 g (10.1 mols) of 3-chloropropyltrimethoxysilane and 766 g (10.1 mols) of thiourea were introduced into a 6-liter double-jacketed glass round bottom flask which was equipped with a stirrer, a reflux cooler, a temperature sensor and a gas feed tube. The mixture was heated to 110° C. while stirring and caused to react by introduction of ammonia at that temperature. After 48 hours the reaction was terminated and the reaction mixture was worked-up. Based on the amount of 3-chloropropyl-trimethoxysilane provided, the yield of 3-mercaptopropyl-trimethoxysilane was 77%.

EXAMPLE 2

Example 1 was repeated in the same apparatus and with the same amounts of starting materials, but 200 g of dimethylformamide were added to the reaction mixture. After a reaction period of 7 hours, gas-chromatographic analysis showed that no more 3-chloropropyl-trimethoxysilane was present in the reaction mixture. Distillative work-up of the reaction mixture produced a yield of 78% 3-mercaptopropyltrimethoxysilane, based on the amount of 3-chloropropyltrimethoxysilane provided.

EXAMPLE 3

2,000 g (10.1 mols) of 3-chloropropyltrimethoxysilane and 566 g (10.1 mols) of sodium hydrogen sulfide together with 400 ml methanol were introduced into the apparatus described in Example 1.

While stirring, the mixture was heated and at the same time methanol was distilled off under a water aspirator pump vacuum until the temperature in the flask rose to 110° C. At this temperature the reaction was allowed to proceed; control samples of the reaction mixture were taken hourly from the flask and were gas chromatographically analyzed. It was found that the reaction subsided after about 5 hours, that a reaction degree of about 65% was achieved and that the yield of target product was about 47%, based on the reacted amount of starting material.

EXAMPLE 4

Example 3 was repeated in the apparatus described in Example 1, except that 80 g of tetrabutylammoniumbromide were added to the mixture in the flask. After 2 hours of reaction time only 4% of the provided amount of silane had reacted, and the reaction was therefore terminated.

EXAMPLE 5

2,000 g (8.8 mols) of 2-chloroethyltriethoxysilane and 670 g (8.8 mols) of thiourea were introduced into the apparatus described in Example 1, and the mixture was reacted in the manner described in Example 1. The unreacted ammonia gas passing through the reaction medium was strongly contaminated with ethylene originating from the B-decomposition of the 2-chloroethyltriethoxysilane. The yield of 2-mercaptoethyltriethoxysilane determined by gas chromatographic analysis was about 24%, based on the provided amount of silane reactant.

EXAMPLE 6

2,000 g (6.35 mols) of p-bromophenyltrimethoxysilane, 485 g (6.35 mols) of thiourea and 400 ml of dimethylformamide were introduced into the apparatus described in Example 1, and the mixture was reacted in the manner described in Example 1. After 48 hours of reaction, p-mercaptophenyltrimethoxysilane could not be identified in the reaction mixture.

EXAMPLE 7

2,000 g (8.6 mols) of 1,3-dichloropropyltrimethoxysilane and 1,307 g (8.6 mols) of thiourea were introduced into the apparatus described in Example 1, and the mixture was reacted in the manner described in Example 1. The reaction was terminated after 48 hours, and the reaction mixture was worked-up. 1,3-dimercaptopropyltrimethoxysilane could not be detected in the reaction mixture.

B) Examples Illustrating the Method According to the Present Invention

EXAMPLE 8

566 g (10.1 mols) of sodium hydrogen sulfide together with 2,400 g of dimethylformamide were introduced into the apparatus described in Example 1. While stirring, 2,000 g (10.1 mols) of 3-chloropropyltrimethoxysilane were added to the contents of the flask over a period of 60 minutes, whereby the temperature of the contents of the flask rose to about 100° C. By application of additional heat the temperature was increased to 110° C. and maintained at this level. Samples of the reaction mixture were taken at intervals of 15 minutes and gas-chromatographically analyzed. After the elapse of 75 minutes of reaction time only traces of the provided silane compound could be detected in the reaction mixture. The distillative work-up of the raw reaction mixture gave a yield of 84% of 3-mercaptopropyltrimethoxysilane.

EXAMPLE 9

493 g (8.8 mols) of sodium hydrogen sulfide together With 2,400 g of dimethylformamide were introduced into the apparatus described in Example 1. 2,000 g (8.8 mols) of 2-chloroethyltriethoxysilane were added to the flask contents over a period of 10 minutes by means of a dropping funnel, accompanied by stirring, whereby the temperature of the flask contents rose to 90° C. By application of additional heat the temperature of the flask contents was increased to 110° C. and was held at this level for 11 hours. At a reaction degree of about 98%, the yield of 2-mercaptoethyltriethoxysilane was 79%.

EXAMPLE 10

566 g (10.1 mols) of sodium hydrogen sulfide together with 2,400 g of dimethylformamide were introduced into the apparatus described in Example 1. 1,844 g (10.1 mols) of 3-chloropropylmethyldimethoxysilane were added to the contents of the flask over a period of 30 minutes, accompanied by stirring. The temperature of the contents of the flask rose to 100° C., and by application of additional heat V the temperature of the flask contents was maintained at 110° C. for 2 hours, whereupon the reaction mixture was gas chromatographically analyzed. At a reaction degree of more than 98%, the yield of 3-mercaptopropylmethyldimethoxysilane was more than 76%.

EXAMPLE 11

356 g (6.35 mols) of sodium hydrogen sulfide together with 1,500 g of dimethylformamide were introduced into the apparatus described in Example 1. 2,000 g (6.35 mols) of p-bromophenyltrimethoxysilane were added to the flask contents over a period of 30 minutes, while stirring, whereby the temperature of the contents of the flask rose to 95° C. After a reaction time of only 3 hours at 110° to 130° C., p-mercaptophenyltrimethoxysilane could be detected in the reaction mixture by gas chromatographic analysis.

EXAMPLE 12

730 g (13.0 mols) of sodium hydrogen sulfide together with 2,400 g of dimethylformamide were introduced into the apparatus described in Example 1. 1,515 g (6.5 mols) of I,3-dichloropropyltrimethoxysilane were added to the contents of the flask over a period of 90 minutes, while stirring and cooling the mixture so that the temperature in the flask did not rise above 100° C. The reaction was allowed to continue to completion at 110° C., and the reaction mixture was then worked-up. The yield of 1,3-dimercaptopropyltrimethoxysilane was 76.2%, based on a 95% degree of reaction.

EXAMPLE 13

730 g (13.0 mols) of sodium hydrogen sulfide together with 2,400 g of dimethylformamide were introduced into the apparatus described in Example 1. 1,593 g (6.5 mols) of bis(3-chloropropyl)dimethoxysilane were added to the flask contents over a period of 45 minutes, while stirring, whereby the temperature in the flask rose-to 84° C. The reaction mixture was allowed to react for 3.5 hours at 120° C., whereupon the reaction mixture was worked-up. Based on a degree of reaction of 99%, the yield of bis(3-mercaptopropyl)dimethoxysilane was 86%.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. In the method of preparing a mercaptosilane of the formula $$(HS)_a-R-\underset{R_p^2}{Si(OR^1)_{3-p}} \text{ or } [(HS)_z-R-]_b\underset{R_q^2}{Si}-(OR^1)_{3-q-(b-1)}$$

wherein
R is alkylene of 1 to 8 carbon atoms, alkarylene, arylalkylene, or aryl,
$R^1$ is alkyl of 1 to 6 carbon atoms which may be interrupted by oxygen atoms, or aryl,
$R^2$ is alkyl of 1 to 8 carbon atoms, aryl, alkaryl, or aralkyl,
p is a whole number from 0 to 3, inclusive,
a is a whole number from 1 to 3, inclusive,
b is 2 or 3, and
q is 0, 1 or 2,
provided the sum of b+q is equal to or less than 4, by reacting a compound of the formula $$(X)_z-R-\underset{R_p^2}{Si(OR^1)_{3-p}} \text{ or } [(X)_a-R-]_b\underset{R_q^2}{Si}-(OR^1)_{3-q-(b-1)}$$

wherein
X is chlorine or bromine, and
R, $R^1$, $R^2$, a, b, p and q have the meaning previously defined,
with an alkali metal hydrogen sulfide, the improvement which comprises performing the reaction in the presence of a polar, aprotic solvent medium.

2. The method of claim 1, wherein the polar, aprotic medium is an N,N-disubstituted dialkylacylamide.

3. The method of claim 2, wherein the polar, aprotic solvent medium is dimethylformamide.

4. The method of claim 1, wherein the polar, aprotic solvent medium is used in an amount from 50 to 100 vol.-%, based on the volume of silane starting material which is used.

5. The method of claim 1, wherein the reaction is performed in the temperature range from 0 to 140° C.

6. The method of claim 5, wherein the temperature range is from 100 to 120° C.

7. The method of claim 5, wherein the silane and the alkali metal hydrogen sulfide are reacted in a molar ratio of 1:1.

* * * * *

UNITED STATES PATENT AND TRADEMARK OFFICE
CERTIFICATE OF CORRECTION

PATENT NO. : 5,107,009
DATED : April 21, 1992
INVENTOR(S) : Hartwig Rauleder et al It is certified that error appears in the above-identified patent and that said Letters Patent is hereby corrected as shown below:

Column 7, line 12, delete "V".

Column 8, line 13, "$(HS)_z$" should read --$(HS)_a$--.

Column 8, line 30, "$(X)_z$" should read --$(X)_a$--.

Signed and Sealed this

Nineteenth Day of October, 1993

BRUCE LEHMAN

Attesting Officer    Commissioner of Patents and Trademarks